United States Patent [19]

Dard et al.

[11] Patent Number: 5,762,499
[45] Date of Patent: Jun. 9, 1998

[54] DENTAL ROOT IMPLANT

[75] Inventors: Michel Dard, Griesheim; Gérard De Witte, Chateauneuf sur Isere, both of Germany; Philippe Rouvre, Toulon, France

[73] Assignee: Merck Patent Gesellschaft mit beschrankter Haftung, Darmstadt, Germany

[21] Appl. No.: 667,516

[22] Filed: Jun. 21, 1996

[30] Foreign Application Priority Data

Jun. 24, 1995 [DE] Germany .......... 195 23 038.8

[51] Int. Cl.⁶ .................................. A61C 8/00
[52] U.S. Cl. .................................. 433/173
[58] Field of Search .................. 433/173, 174, 433/175, 172, 176

[56] References Cited

U.S. PATENT DOCUMENTS

| 2,857,670 | 10/1958 | Kiernan, Jr. | 433/175 |
| 3,590,485 | 7/1971 | Chercheve | 433/174 |
| 5,007,835 | 4/1991 | Valen | 433/174 |
| 5,078,607 | 1/1992 | Niznick | 433/174 |

FOREIGN PATENT DOCUMENTS 1305478 1/1973 United Kingdom ........ 433/173

*Primary Examiner*—Cary E. O'Connor
*Attorney, Agent, or Firm*—Millen, White, Zelano, & Branigan, P.C.

[57] ABSTRACT

A dental root implant has a metal implant body which has transverse openings near its rounded lower end. The implant body has a shape which tapers downwards. Circumferential grooves are arranged parallel and mutually separated in its outer face, the grooves being rounded at their bases and at the junctions with neighboring outer face sections.

8 Claims, 2 Drawing Sheets

1

DENTAL ROOT IMPLANT

FIELD OF THE INVENTION

The invention relates to a dental root implant having a metal implant body which has transverse openings near its rounded lower end.

BACKGROUND ART

There are various known ways of producing dental root implants of this type. The implant body is fitted into a tooth socket of the jaw, prepared for this purpose by drilling, and is used for applying a dental prosthesis. By way of example, two implant bodies may support a dental bridge.

The shape of the implant body should be chosen in such a way that, on the one hand, a good fit is ensured with the least possible intervention on the bone in the region of the tooth socket and, on the other hand, secure anchoring of the implant body in the bone should be ensured.

With most known dental root implants, effective immediate anchoring in the jaw bone is highly desired. To this end, the implant bodies are provided with screw threads, having relatively sharp edges, which make it possible to screw into the jaw bone. However, it has been found with this configuration of the implant body that the bone tissue recedes at the sharp edges of the implant body, under the effect of the stresses which occur, so that the originally firm mechanical connection between the implant body and the jaw bone deteriorates over time.

Although a smooth external shape of the implant body does not exhibit these disadvantages, a sufficiently firm connection with the jaw bone is not in this case ensured, in spite of the holes into which the regrowing bone tissue penetrates.

Other known implant bodies have rounded circumferential grooves on a cylindrical outer face. However, preparing the tooth socket for this purpose makes it necessary to remove a relatively large amount of bone material.

SUMMARY OF THE INVENTION

The object of the invention is to develop a dental root implant of the generic type mentioned at the outset in such a way that good anchoring of the implant body in the jaw bone is achieved with the least possible requirement in preparing the tooth socket and thus also with the least possible surgical intervention.

This object is achieved according to the invention in that the implant body has a shape which tapers downwards and in that circumferential grooves are arranged parallel and mutually separated in its outer face, these grooves being rounded at their base and at the junction with the respectively neighboring outer fact sections.

By virtue of the arrangement of the circumferential grooves, an increase in the external surface area compared to a smooth outer face is achieved which is so great that an essentially improved anchoring of the dental root implant in the jaw is thereby ensured. Only by combining this surface area increase, obtained by virtue of the circumferential grooves, with the rounded configuration of all edges and junctions is the effect achieved that the bone tissue completely fills the base of the groove on the one hand, an does not recede at the outer edges, even under the stresses which act over time, on the other hand. In further combination with the shape of the implant body, which tapers downwards, a particularly good fit to the natural shape of the tooth socket is achieved, as a result of which the requirement for preparing the tooth socket is essentially reduced and, in particular, the surgical intervention on the bone is reduced to a minimum.

An embodiment in which the outer face sections between neighboring circumferential grooves are wider than the circumferential grooves has been found to be a particularly favorable distribution of the circumferential grooves. These outer face sections are preferably approximately twice as wide as the circumferential grooves.

Upon further study of the specification and appended claims, further objects and advantages of this invention will become apparent to those skilled in the art.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION

Figure 1:
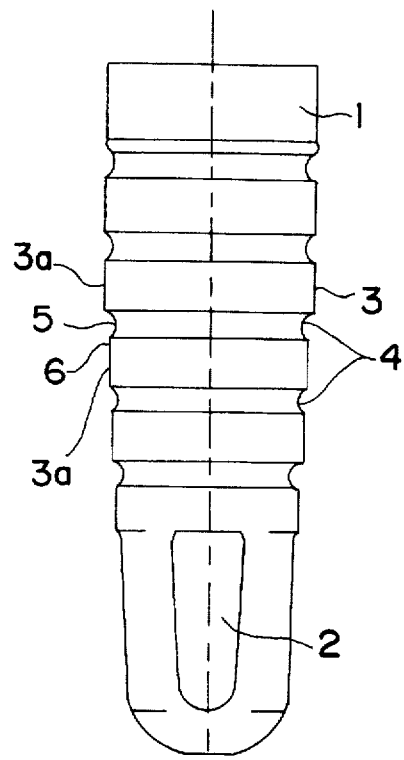
FIG. 1 shows a side view of the implant body of a dental root implant.
Figure 2:
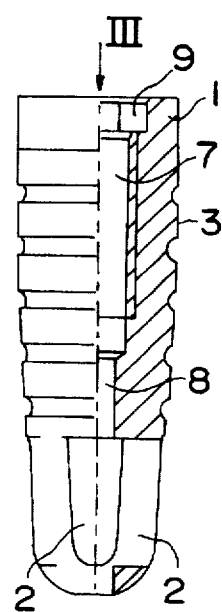
FIG. 2 shows the implant body according to FIG. 1 on a smaller scale and half in longitudinal section.
Figure 3:
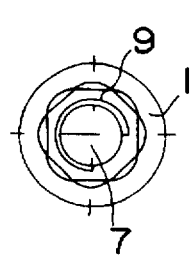
FIG. 3 shows a view in the direction of the arrow III in FIG. 2.

The implant body 1, represented in FIGS. 1–3, and serving as a dental root implant, consists of metal, preferably a titanium alloy such as $TiAl_6V_4$. It has a shape which tapers downwards and is therefore matched to the shape of the receiving tooth socket in the jaw.

At its rounded lower end, the implant body 1 has two transverse openings 2, at right angles to each other, which are tapered downwards to approximately the same extent as the implant body 1.

Circumferential grooves 4 are arranged, parallel and mutually separated, in the outer face 3 above the openings 2. These circumferential grooves 4 are rounded at their base 5 and at their edges 6 forming the junction with the respectively neighboring outer face sections 3a. This produces an outer face 3 of the implant body 1 which is designed overall without sharp edges but its surface area is nevertheless substantially larger than that of a flat tapered body with comparable dimensions. This surface area enlargement, in combination with the tapered shape and the strict avoidance of sharp edges, leads to a particularly effective and long-lasting connection with the surrounding bone tissue when the implant body 1 is fitted in a tooth socket of a jaw.

In the preferred illustrative embodiment which is represented, the outer face sections 3a between neighboring circumferential grooves 4 are wider than these circumferential grooves 4, and actually preferably approximately twice as wide as the circumferential grooves 4.

As represented in FIG. 2, the implant body 1 has a central threaded bore 7 at its upper end which protrudes out of the jaw, and in the illustrative embodiment represented, this threaded bore joins with the openings 2 via a bore 8. The central bore is provided with an internal octagon 9 at the outer end of the threaded bore 7.

Figure 4:
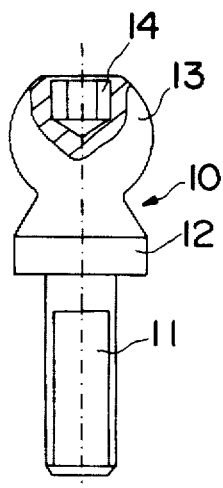
FIG. 4 shows a manipulation head which can be screwed into the implant body according to FIGS. 1–3.

The manipulation head 10 represented in FIG. 4 is provided for manipulating the implant body 1, in particular during fitting into the jaw and also for removal from the jaw. This manipulation head has a threaded post 11, which can be screwed into the threaded bore 7 and to which a spherical head 13 is jointed by an intermediate piece 12, this spherical head 13 being provided at its upper end with an internal hexagon 14 for engaging a screwdriver. With a retention tool which is matched to it, the spherical head 13 makes it possible to manipulate the implant body 1 in any angular position.

Figure 5:
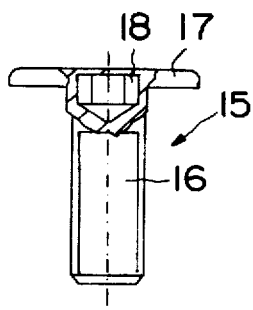
FIG. 5 shows a flat-headed obturation screw which can be screwed into the implant body.

After the implant body 1 has been fitted into a pre-prepared tooth socket using the manipulation head 10, it is closed off using an obturation screw 15 such as represented in FIG. 5. The obturation screw 15 has a threaded post 16 and a flat head 17 which has approximately the same external diameter as the upper end of the implant body 1. A central internal hexagon 18 is also used in this case for the engagement of a screwdriver for screwing the obturation screw into the implant body 1.

Figure 6:
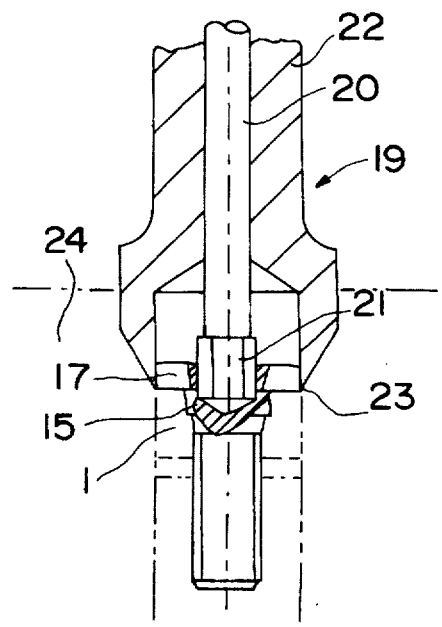
FIG. 6 shows an extraction tool, for extracting the gingiva in the region of the dental root implant, fitted to an obturation screw according to FIG. 5.

After the implant body 1 has been incorporated into the jaw and the gingiva has healed over the flat head 17 of the obturation screw 15, the extraction tool 19 represented in longitudinal section in FIG. 6 is engaged. The internal hexagon 18 of the obturation screw 15 forms a central engagement opening for receiving a centering and guide pin 20 which has a mating external hexagon 21 at its lower end. A punch 22 is guided displaceably along the centering and guide pin 20 and has at it slower end an annular edge 23 whose diameter corresponds to the external diameter of the head 17 of the obturation screw 15.

Figure 7:
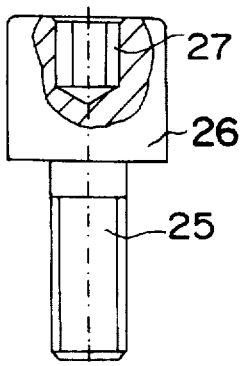
FIG. 7 shows a cicatrization head which can be screwed into the implant body.

After the centering and guide pin 20 has been engaged on the obturation screw 15, a circular hole whose internal diameter approximately corresponds to the external diameter of the head 17 of the obturation screw 15 is extracted from the surrounding gingiva 24 using the punch 22. The obturation screw 15 is then screwed out from the implant body 1 and the screw represented in FIG. 7 is screwed in its place using its threaded post 25 which is provided with a cicatrization head 26. The cicatrization head 26 has, like the head 17 of the obturation screw 15, at least approximately the same external diameter as the upper end of the implant body 1. The height of the cicatrization head 26 is such that it protrudes from the gingiva 24 and has the effect that an approximately cylindrical hole, through which a dental prosthesis can finally be screwed onto the implant body 1, heals in the gingiva 24. The cicatrization head 26 likewise has an internal hexagon 27 for screwing in and out.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A dental root implant comprising:
a metal implant body with transverse openings (2) near a lower rounded end thereof, the implant body (1) tapering toward a distal end and having circumferential grooves (4) arranged in parallel therein and being mutually separated at outer face (3) thereof, the grooves having rounded bases and being rounded at junctions (6) with respectively neighboring outer face sections (3a), wherein the transverse openings (2) are tapered downwards at approximately the same extent as the implant body (1).

2. The dental root implant according to claim 1, wherein the outer face sections (3a) between neighboring circumferential grooves (4) are wider than the circumferential grooves (4).

3. The dental root implant according to claim 2, wherein the outer face sections (3a) between neighboring circumferential grooves (4) are approximately twice as wide as the circumferential grooves (4).

4. The dental root implant according to claim 1, wherein the implant body (1) has a central threaded bore (7) at its upper end, into which a manipulation head (10), an obturation screw (15) with a flat head (17) and a cicatrization head (26) are adapted to be screwed.

5. The dental root implant according to claim 4, wherein the manipulation head (10) has a spherical end surface (13).

6. The dental root implant according to claim 4, wherein the obturation screw (15) has a central engagement aperture (18) for receiving a centering and guide pin (22) on which a punch (22) which has an annular edge (23) corresponding to the external diameter of the head (17) of the obturation screw (15) is adapted to be guided.

7. The dental root implant according to claim 4, wherein the head (17) of the obturation screw (15) and the cicatrization head (26) has at least approximately the same external diameter as the upper end of the implant body (1).

8. The dental route implant according to claim 4, wherein the central threaded bore (7) connects with the transverse openings (2).

* * * * *